(12) United States Patent
Bruns

(10) Patent No.: US 7,160,276 B2
(45) Date of Patent: Jan. 9, 2007

(54) WEARABLE URINE RECEIVING AND STORAGE DEVICE

(76) Inventor: Dennis Bruns, 6745 Harlan Dr., Eden Prairie, MN (US) 55346

( * ) Notice: Subject to any disclaimer, the term of this patent is extended or adjusted under 35 U.S.C. 154(b) by 279 days.

(21) Appl. No.: 10/282,295

(22) Filed: Oct. 28, 2002

(65) Prior Publication Data

US 2004/0082926 A1 Apr. 29, 2004

(51) Int. Cl.
*A61F 5/44* (2006.01)
(52) U.S. Cl. .................. 604/346; 604/339; 604/349; 604/353
(58) Field of Classification Search .............. 604/327, 604/329, 346, 347, 349, 350, 351, 353, 355
See application file for complete search history.

(56) References Cited

U.S. PATENT DOCUMENTS

| | | | | |
|---|---|---|---|---|
| 3,526,227 A | * | 9/1970 | Appelbaum | 604/350 |
| 4,117,845 A | * | 10/1978 | Brown | 604/327 |
| 4,713,067 A | * | 12/1987 | Rothenberg et al. | 604/353 |
| 4,846,816 A | * | 7/1989 | Manfredi | 604/323 |
| 5,084,037 A | * | 1/1992 | Barnett | 604/349 |
| 5,618,277 A | * | 4/1997 | Goulter | 604/349 |
| 5,662,631 A | * | 9/1997 | Marx | 604/352 |
| 6,068,618 A | * | 5/2000 | Anderson | 604/349 |
| 6,248,096 B1 | * | 6/2001 | Dwork et al. | 604/349 |
| 6,532,604 B1 | * | 3/2003 | Moser | 4/450 |
| 6,613,027 B1 | * | 9/2003 | Kulikov | 604/353 |
| 6,682,511 B1 | * | 1/2004 | Besoyan | 604/353 |
| 6,732,384 B1 | * | 5/2004 | Scott | 4/144.3 |
| 2003/0018321 A1 | * | 1/2003 | Rosenblum | 604/544 |
| 2003/0032931 A1 | * | 2/2003 | Grundke et al. | 604/349 |
| 2003/0195484 A1 | * | 10/2003 | Harvie | 604/355 |
| 2004/0176731 A1 | * | 9/2004 | Cheng et al. | 604/329 |

\* cited by examiner

*Primary Examiner*—Tatyana Zalukaeva
*Assistant Examiner*—Michael G. Bogart
(74) *Attorney, Agent, or Firm*—Pauly, DeVries Smith & Deffner L.L.C.

(57) ABSTRACT

A device for receiving and retaining urine from a person wearing the device is disclosed. The device is particularly well suited for use by persons who expect to have inadequate access to bathroom facilities, such as people pursuing recreational activities or attending large public gatherings, as well as persons who have a greater than normal need for access to a bathroom, such as people with diabetes. The device provides a sleek, streamlined form that is comfortable to wear, as well as being discrete and readily concealed by a user.

1 Claim, 5 Drawing Sheets

WEARABLE URINE RECEIVING AND STORAGE DEVICE

FIELD OF THE INVENTION

The present invention is directed to a wearable device for receiving and storing urine. In particular, the invention is directed to a device that receives urine from a person, such as a golfer, boater or hiker, and retains the urine until it can be properly disposed of in a bathroom facility.

BACKGROUND

Many people enjoy activities that take them into the outdoors, to sporting events, hiking paths, and other places where they do not have ready access to bathroom facilities. For example, it is common for golf courses to have just a couple of bathroom facilities, typically far apart on the course, located such that a golfer might play an hour or more without access to a bathroom. Similarly, many public walking paths and parks do not have adequate bathroom facilities, if they have any such facilities at all. When they do have bathrooms, the number is often too few to meet the demand or they are not located in all areas of the park or trail. Also, hygiene is often a problem, particularly when the bathroom facilities are not frequently cleaned. This is a particular problem with portable toilet facilities set up for seasonal use and for large events, such as concerts and fairs.

In addition to recreational activities, many occupations are inherently challenging from the standpoint of bathroom facilities. This is true with many traveling occupations, such as bus drivers who must keep a regular schedule of stops, and truck drivers who get paid based upon miles driven. Neither of these occupations (for example) allow frequent stops for bathroom breaks or for unscheduled bathroom breaks. Construction workers have similar problems, as do sales staff in small businesses that have only one person staffing a store. Such stores often have to close for a few minutes when their attendant needs to take a break to use a bathroom. Also, some such stores do not even have their own bathrooms, so the attendant has to go off site to find a suitable bathroom to use.

Under these circumstances, whether they are recreational or occupational, people often solve the problem of bathroom access with one of two approaches: either they carefully choose their activities to avoid needing a bathroom in an inaccessible location, or they try to find a private, but generally unapproved, location to relieve themselves. In the first case, people may avoid golfing, hiking, walking, or other sporting and recreational pursuits if they believe they will be unable to have access to bathroom facilities. In the second case, people will either discretely seek to find a private wooded location to use as a bathroom, or in rare instances be less discrete in using public or private property to relieve themselves.

The problems of inadequate access to bathroom facilities are certainly a considerable problem for many people who have recreational pursuits or occupations that take them away from bathrooms. However, the problem is even more severe for people who have medical conditions that necessitate that they use a bathroom more frequently to urinate than normal individuals. For example, people with diabetes sometimes have increased needs to use a bathroom, as do people with small bladders. For these individuals, the lack of ready access to adequate bathrooms can be a tremendous problem. An aging population makes this problem ever more common.

Thus, a need exists for a solution to the problem of inadequate bathroom access for people in remote locations, with occupations that limit access to bathrooms, and for individuals who have a need for more frequent access to a bathroom.

SUMMARY OF THE INVENTION

The present invention is directed to a device for receiving and retaining urine from a person wearing the device. The device is particularly well suited for use by persons who expect to have inadequate access to bathroom facilities, such as people pursuing recreational activities or large public gatherings, people working outdoors, as well as persons who have a greater than normal need for access to a bathroom, such as people with diabetes. The device is designed to be easy to use and relatively inconspicuous.

In one implementation, the device comprises a urine receiving receptacle configured and arranged for receiving a penis, an expandable bladder configured and arranged to receive liquid urine from the receiving receptacle, the expandable bladder containing an input for receiving liquid urine and an output for discharging liquid urine; plus a passage connecting the urine receiving receptacle to the expandable bladder; and a flexible retainer secured to the urine receiving receptacle, the retainer configured to be fastened around the waist of the user with a strap to hold the receptacle in place on the user.

In an alternative implementation, the device is a unisex device, where the device can be used by either a man or a woman, that comprises a urine receiving receptacle forming an elongate flexible pouch having a front end, a back end, a first side, and a second side. The first and second sides define an upper edge of the pouch, and the pouch is wider in its center than at either of the first and second ends. The pouch is typically configured and arranged such that it is wider near the front end than near the back end, and the pouch is sufficiently large so as to retain a male's penis (and scrotum in some implementations). When installed upon a user, the upper edge of the pouch makes contact with the user's skin, thereby forming a seal around the edge of the pouch. An expandable bladder receives liquid urine from the receiving receptacle. The expandable bladder contains an input for receiving liquid urine and an output for discharging liquid urine. A passage connects the urine receiving receptacle to the expandable bladder. A flexible retainer is secured to the urine receiving receptacle, the retainer configured with a waist strap to be fastened around the waist of the user and to hold the receptacle in place on the user such that the receptacle forms a snug seal around the opening of the urethra of either a male or a female user such that urine does not readily pass across the seal during normal use. Generally, the pouch is configured and arranged such that the passage connecting the urine receiving receptacle to the expandable bladder is joined to the urine receiving receptacle at a lowest point in the receptacle when the receptacle is worn by a user.

In some implementations of this embodiment, both ends of the pouch have multiple loops configured for receiving the flexible retainer so as to make the device adjustable for patients of different sizes. Excess loops can be removed from the device to make it smaller and more comfortable. Also, the pouch can be made of a breathable material, such as an expanded polytetrafluoroethylene (PTFE) material, commonly sold as Gore-Tex.

Also, in some implementations, both for the male-only device and the unisex device, a second passage is provided. The second passage connects the expandable bladder to a dispenser distant from the bladder, the dispenser configured and arranged to be positioned near the foot of a patient, for example. This dispenser can include a valve.

The device is typically installed such that the expandable bladder is retained at a user's waist level or below, typically by bands or straps that hang from a wearer's waist. It is usually desirable to have the device be as comfortable as possible, while still providing ready capture of urine within the receptacle and transfer of the urine into the expandable bladder. Also, it is desirable that the device be as comfortable and non-intrusive as possible.

Other features and advantages of the invention will be apparent from the following detailed description of the invention and the claims. The above summary of principles of the disclosure is not intended to describe each illustrated embodiment or every implementation of the present disclosure. The detailed description that follows more particularly exemplifies certain embodiments utilizing the principles disclosed herein.

FIGURES

Figure 1:
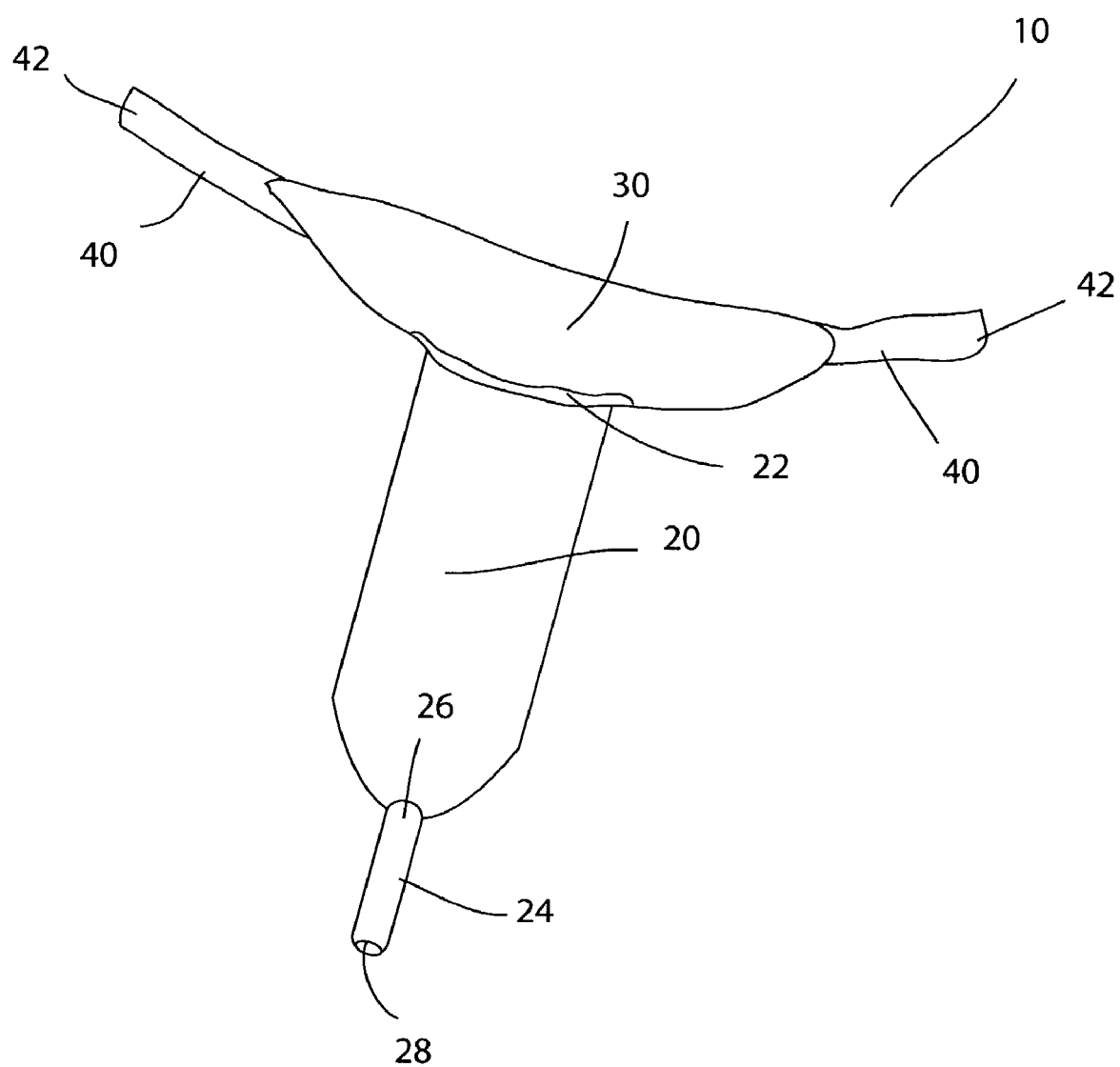
FIG. 1 is a perspective view of a portion of a first urine retention device constructed and arranged in accordance with a first implementation of the invention, showing a receptacle for the urine, the device configured and arranged for use by a male.

While principles of the invention are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure and claims.

DETAILED DESCRIPTION OF THE INVENTION

This invention is directed to a device for receiving and retaining urine from a person wearing the device. The device is particularly well suited for use by persons who expect to have inadequate access to bathroom facilities, such as people pursuing recreational activities or large public gatherings, as well as persons who have a greater than normal need for access to a bathroom, such as people with diabetes.

The device is unique in that it provides a sleek, streamlined form that is comfortable to wear, as well as being discrete and readily concealable by a user. The device is primarily suited for use by individuals whose urinary tracts typically function normally, but who occasionally find themselves in situations where their bladder will not hold as much urine as necessary, such as at sporting events, during exercise, etc. Thus, users usually do not have an incontinence problem, but the invention is also suitable for such people with incontinence.

One of the significant benefits of the present invention is that it provides improved mobility for users over prior urine collection systems, and is also extremely comfortable to wear, while avoiding excessive use of straps or cords to retain the device in place. Various implementations of the invention are possible, including devices that are suitable only for use by men and devices that are suitable for use by both men and women. Also, the size of the device can be changed to accommodate different size individuals so that a "one size fits all" product can be made. The device is designed so that it will only be used by one user, but the one size fits all characteristics allow a retailer to stock just one product rather than multiple products. In some implementations all or part of the device is disposable, while in other implementations the entire device is reusable.

In one implementation, the device comprises a urine receiving receptacle configured and arranged for receiving a penis, and an expandable bladder configured and arranged to receive liquid urine from the receiving receptacle. The expandable bladder contains an input for receiving liquid urine and an output for discharging liquid urine; plus a passage (normally a thin hose or tube) connecting the urine receiving receptacle to the expandable bladder. A flexible retainer is secured to the urine receiving receptacle, and the retainer is configured to be fastened around the waist of the user via a waist strap to hold the receptacle in place on the user. Generally, the receptacle is configured and arranged such that the passage connecting the urine-receiving receptacle to the expandable bladder is joined to the urine receiving receptacle at a lowest point in the receptacle when the receptacle is worn by a user.

Reference will now be made to the Figures. FIG. 1 shows a partial perspective view of a urine-retaining device 10 constructed and arranged in accordance with the invention. Urine-retaining device 10 includes a penis-retaining receptacle 20 configured to comfortably retain a penis. Device 10 also includes a base 30 onto which the receptacle 20 is attached, typically along an overlapping area 22 where the receptacle 20 and base 30 can be fused together by heat, adhesive, mechanical means, etc. The base 30 also includes straps 40, which are only partially depicted with ends 42, but typically are sufficiently long that they reach around a person wearing the device 10 to keep it in place, in particular to retain a person's penis within receptacle 20. Receptacle 20 also includes a drain hole 26 onto which a tube 24 having end 28 is attached. It will be appreciated that tube 24 is typically much longer than that shown in FIG. 1, but is depicted herein as only a partial representation.

The receptacle 20 is constructed such that it is flexible, but holds it shape even when not in use. Thus, the receptacle 20 is flexible but not readily collapsible, at least it does not collapse under its own weight. This ability to maintain its shape is important because it provides a more comfortable device and also helps in keeping the device clean because the device readily dries after use (and optionally being washed), whereas easily collapsed receptacles would retain water within the collapsed portions and potentially be a source of germ growth. In certain implementations the base 30 is made of the same material as the receptacle 20, and in such implementations the base 30 is typically integrally formed (such as by injection molding) to the receptacle 20. The base 30 is important because it provides a comfortable location for securing straps that are subsequently secured around the waist of a wearer.

Figure 2:
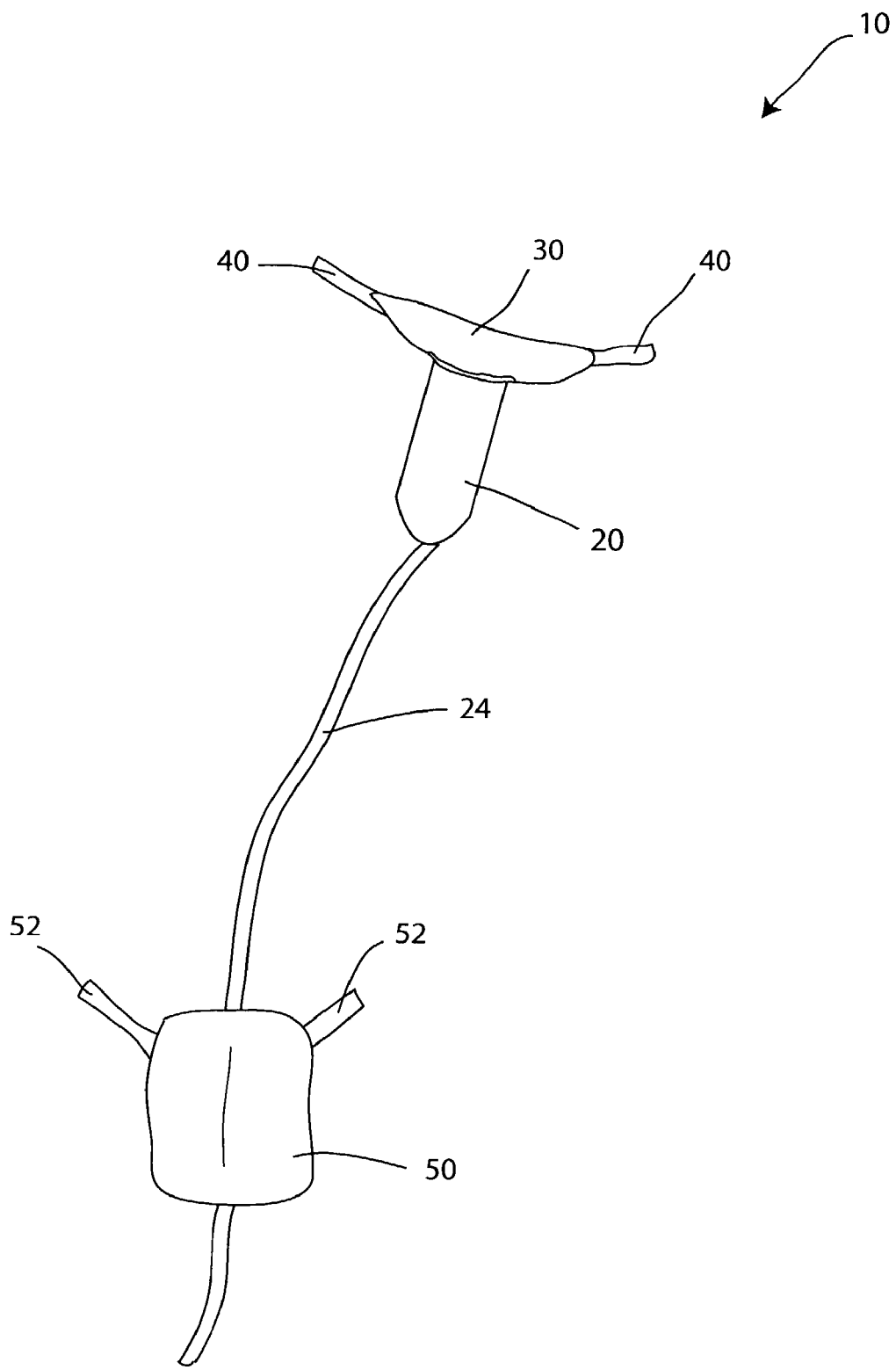
FIG. 2 is a perspective view of the urine retention device of FIG. 1, showing a vessel for retaining the urine.
Figure 3:
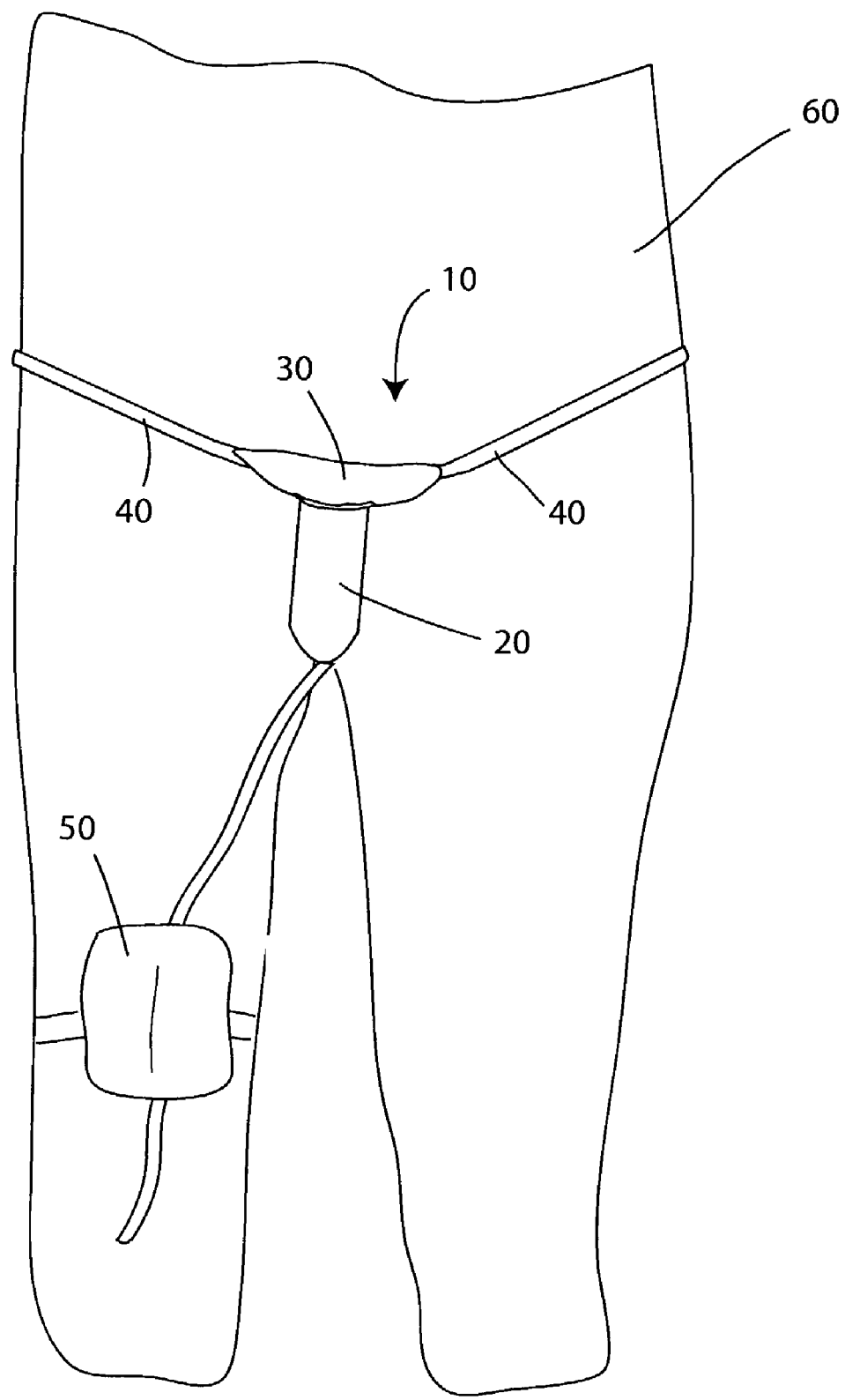
FIG. 3 is a perspective view of the urine retention device of FIGS. 1 and 2, depicting the device installed on a person.

A further view of the device 10 is depicted in FIG. 2, here showing the device along with a urine-retaining bag 50. Also depicted are receptacle 20, base 30, straps 40 to retain upper portions of device 10 around a user's waist, tube 24 and straps 52 to secure the bag 50 to a user. During use the device 10 is secured to a person 60, as shown in FIG. 3. Device 10 is secured around the waist of a user so that the receptacle 20 retains a man's penis. Typically the scrotum is not retained within receptacle 20. Also, urine-retaining bag 50 is positioned below the receptacle 20, and typically is attached to the leg of the user, but can also be attached to the strap 40 around a user's waist. In most implementations the bag 50 contains a backflow valve so that urine cannot travel back from the bag 50 up to the receptacle 20. In this manner it is possible to use the device 10 in sporting activities that will subject bag 50 to movement and pressure changes because the backflow valve prevents urine from returning up tube 24 to receptacle 20.

Figure 4A:
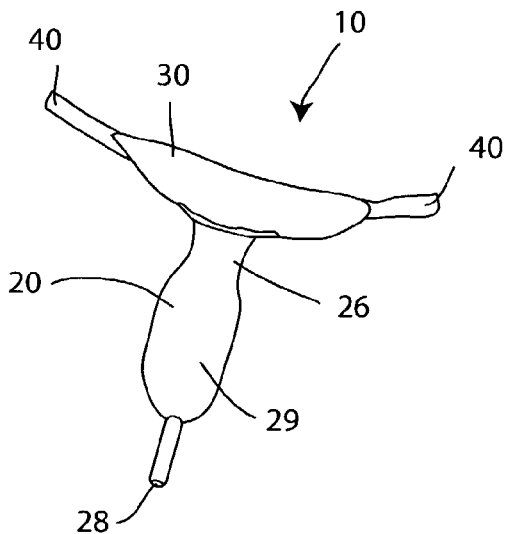
FIG. 4A is a perspective view of an additional implementation of a urine retention device constructed and arranged in accordance with the invention, the device configured and arranged for use by a male.
Figure 4B:
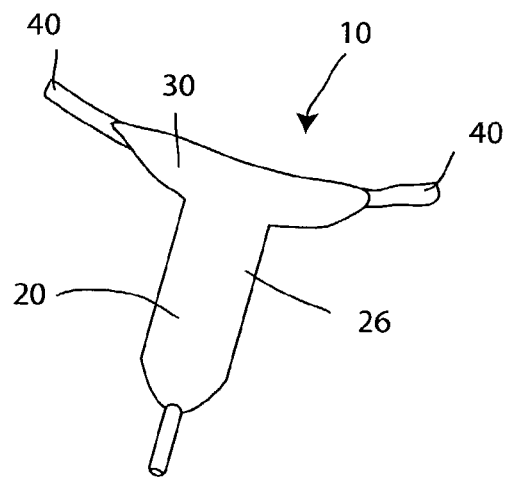
FIG. 4B is a perspective view of an additional implementation of a urine retention device constructed and arranged in accordance with the invention, the device configured and arranged for use by a male.
Figure 4C:
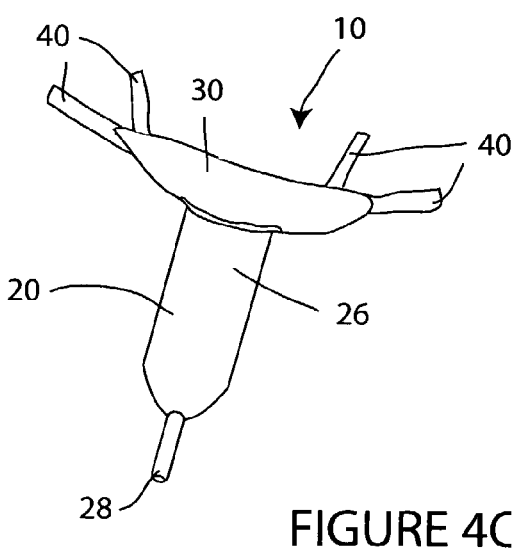
FIG. 4C is a perspective view of an additional implementation of a urine retention device constructed and arranged in accordance with the invention, the device configured and arranged for use by a male.

In reference now to FIGS. 4A, 4B, and 4C, various additional embodiments of the invention are depicted. In FIG. 4A, the receptacle 20 is shown modified such that the upper area 26 near the base 30 is narrower than the lower area 29 near the drain on the receptacle 20. This narrowing of the receptacle 20 provides a more complete seal around a user's penis, thereby further reducing the likelihood of urine escaping from the receptacle 20 before it can be discharged into a urine-receiving bag.

FIG. 4B shows another implementation in which the receptacle 20 and base 30 have been integrally formed out of one piece of material, typically a soft and elastic polymeric material, such as latex rubber or non-latex rubber. Forming the receptacle 20 and base 30 out of one piece can be advantageous because it allows case of manufacture and also removes a joint that can cause chaffing on a user.

FIG. 4C shows yet another implementation of the invention, in which the base 30 is configured such that it has four straps 40 attached to it rather than two. The additional straps can be useful in retaining the device 10 on a patient, particularly during strenuous activities.

Figure 5A:
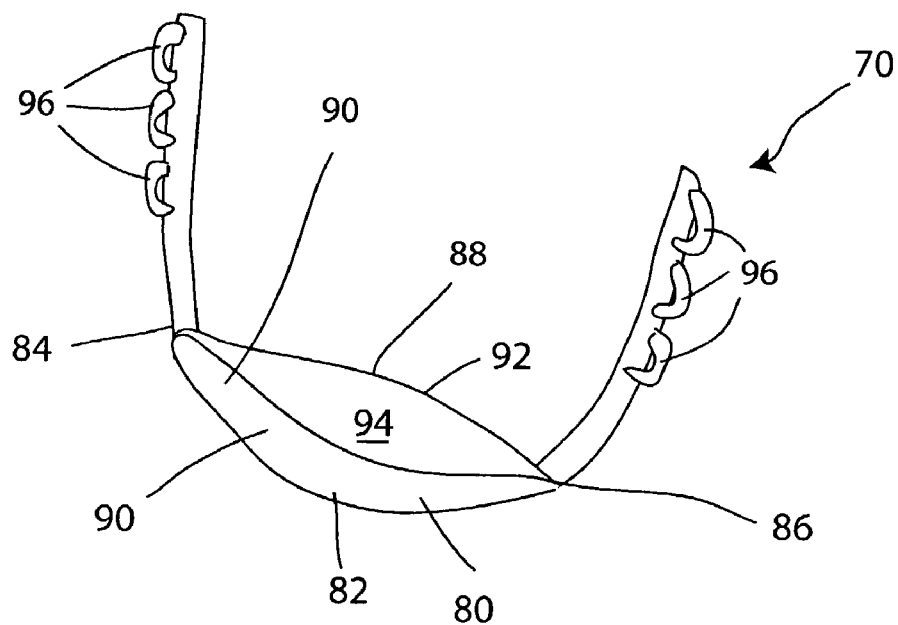
FIG. 5A is a perspective view of a unisex urine retention device constructed and arranged in accordance the invention, the device configured and arranged for use by a male or a female.
Figure 5B:
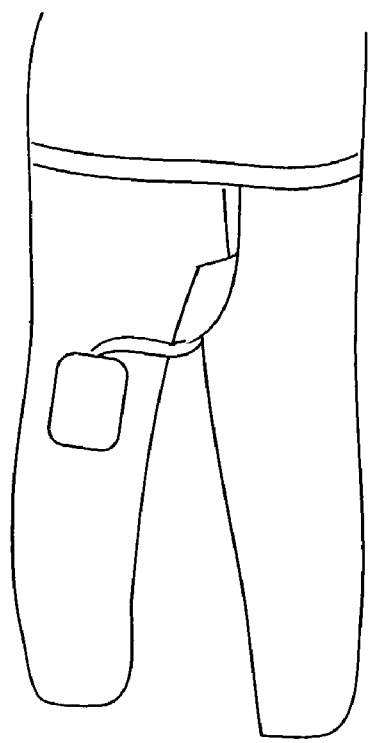
FIG. 5B is a perspective view of an additional embodiment of a unisex urine retention device constructed and arranged in accordance with the invention, the device installed on a user.

As noted above, alternative embodiments of the invention include unisex implementations where the device can be used by either a man or a woman. One such implementation of such a design is shown in FIG. 5A. Device 70 of FIG. 5A shows a urine-receiving receptacle 80 forming an elongate flexible pouch 82 having front end 84, a back end 86, a first side 88, and a second side 90. The first and second sides 88, 90 define an upper edge 92 of the pouch 82, and the pouch 82 is wider in its center 94 than at either of the front and back ends 84, 86. The elongate flexible pouch 82 is sufficiently large to retain a male's penis (and scrotum in some implementations), wherein when installed upon a user the upper edge 92 of the pouch 82 makes contact with the user's skin, thereby forming a seal around the edge of the pouch. Alternatively, when installed on a woman, the pouch 82 fits between the legs of the woman so that the upper edge 92 forms a seal with the opening of the urethra within the edges of the seal, thereby providing an enclosed area for receipt of urine to be channeled to a bladder for retaining it. FIG. 5A further shows multiple loops 96 for adjusting the position of the device 70, and in particular the receptacle 80, on a person. Typically, a user will use one loop on each strap, with large persons using the loops furthest up the straps, and smaller persons using loops nearer the receptacle 80. Excess loops and straps, above the ones being used, can be cut off (such as with a scissors) to make the device as comfortable and inconspicuous as possible. FIG. 5B shows this unisex model installed on a person.

In addition, an expandable bladder (not shown) receives liquid urine from the receiving receptacle, the expandable bladder containing an input for receiving liquid urine and an output for discharging liquid urine. A passage connects the urine receiving receptacle to the expandable bladder. A flexible retainer is secured to the urine receiving receptacle, the retainer configured with a waist strap and fastener to be fastened around the waist of the user and to hold the receptacle in place on the user such that the receptacle forms a substantially snug seal around the opening of the urethra of either a male or a female user so as to prevent leakage of urine.

Generally, the pouch is configured and arranged such that the passage connecting the urine-receiving receptacle to the expandable bladder is joined to the urine-receiving receptacle at a lowest point in the receptacle when the receptacle is worn by a user. It is usually desirable to have the device be as comfortable as possible while still providing ready capture of urine within the receptacle and transfer of the urine into a storage bladder. Also, it is desirable that the device be as non-intrusive as possible.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

I claim:

1. A device for receiving and retaining urine from a male or female user, the device comprising:
    a flexible but not readily collapsible urine receiving receptacle forming an elongate flexible pouch having a front end, a back end, a first side, and a second side, the first and second sides defining an upper edge of the pouch, and the pouch being wider in its center than at either of the front and back ends, and configured and arranged such that the pouch is wider near the front end and than near the back end, the pouch sufficiently large to retain a male's penis (and optionally scrotum), wherein when installed upon a user the upper edge of the pouch makes contact with the user's skin, thereby forming a seal around the edge of the pouch;
    an expandable bladder configured and arranged to receive liquid urine from the receiving receptacle, the expandable bladder containing an input for receiving liquid urine and an output for discharging liquid urine;
    a passage connecting the urine receiving receptacle to the expandable bladder;
    and a flexible retainer secured to the urine receiving receptacle, the retainer configure to be fastened around the waist of the user via a strap to hold the receptacle in place on the user such that the receptacle from a substantially liquid-proof seal around the opening of the urethra of either a male or female user,
    wherein excess loops of the multiple loops are configured to be removed from the device to make the device smaller and more comfortable.

* * * * *